(12) United States Patent
Beck

(10) Patent No.: US 11,571,320 B2
(45) Date of Patent: Feb. 7, 2023

(54) DEFLECTION ELEMENT FOR DEFLECTING TIE CABLES IN OR ON ORTHOPEDIC OR MEDICAL INSTRUMENTS OR SPORTS INSTRUMENTS

(71) Applicant: Bauerfeind AG, Zeulenroda-Triebes (DE)

(72) Inventor: André Beck, Stadtroda (DE)

(73) Assignee: Bauerfeind AG, Zeulenroda-Triebes (DE)

( * ) Notice: Subject to any disclaimer, the term of this patent is extended or adjusted under 35 U.S.C. 154(b) by 33 days.

(21) Appl. No.: 16/077,651

(22) PCT Filed: Feb. 9, 2017

(86) PCT No.: PCT/EP2017/052918
§ 371 (c)(1),
(2) Date: Aug. 13, 2018

(87) PCT Pub. No.: WO2017/140578
PCT Pub. Date: Aug. 24, 2017

(65) Prior Publication Data
US 2019/0053930 A1    Feb. 21, 2019

Related U.S. Application Data

(60) Provisional application No. 62/295,830, filed on Feb. 16, 2016.

(30) Foreign Application Priority Data

Feb. 16, 2016   (DE) .................. 20 2016 100 799.2

(51) Int. Cl.
*A61F 5/00* (2006.01)
*A61F 5/01* (2006.01)

(52) U.S. Cl.
CPC ................ *A61F 5/013* (2013.01); *A61F 5/01* (2013.01); *A61F 2005/0167* (2013.01); *A61F 2005/0169* (2013.01)

(58) Field of Classification Search
CPC ........ A61F 5/01; A61F 5/0132; A61F 5/0125; A61F 5/013; A61F 5/02; A61F 5/022;
(Continued)

(56) References Cited

U.S. PATENT DOCUMENTS 1,507,216 A  *  9/1924  Stockton .................. A41F 1/00
                                                    24/595.1
5,435,563 A  *  7/1995  Salvatore ........... A63B 69/0059
                                                    128/870
(Continued)

FOREIGN PATENT DOCUMENTS

CN         104068954 A      10/2014
CN      000104068954 B       9/2017
(Continued)

OTHER PUBLICATIONS

International Search Report corresponding to PCT/EP2017/052918 dated May 23, 2017.
(Continued)

*Primary Examiner* — Adam Baker
(74) *Attorney, Agent, or Firm* — Carter, DeLuca & Farrell LLP; George Likourezos

(57) ABSTRACT

The invention relates to deflector (100) to deflect rope (130) in orthopedic or medical accessories, or athletic accessories, whereby the deflector comprises at least first subcomponent (110) and second subcomponent (120), whereby first subcomponent (110) and second subcomponent (120) are adjustable, respectively, with only one degree of freedom against one another, and whereby first subcomponent (110) and second subcomponent (120) exhibit, respectively, at
(Continued)

Figure 1:
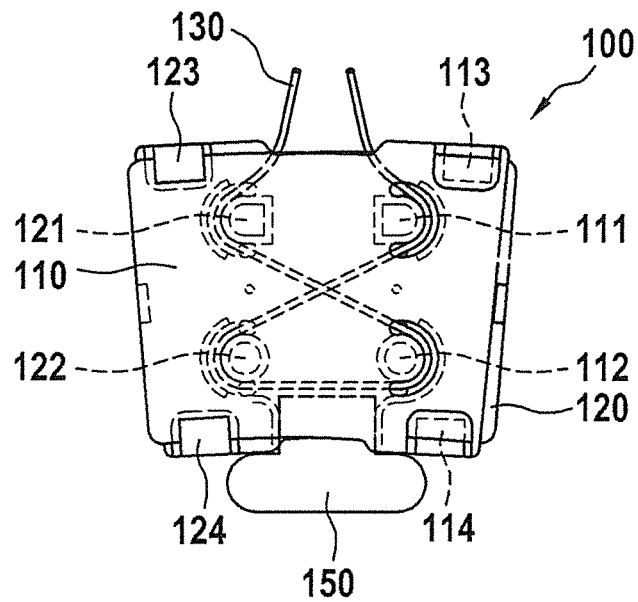

least one rope guidance element (111, 112, 121, 122) to deflect rope (130).

21 Claims, 9 Drawing Sheets

(58) Field of Classification Search
CPC .......... A61F 5/024; A61F 5/026; A61F 5/028; A61F 5/03; A61F 5/0553; A61F 2005/0146; A61F 2005/0148; A61F 2005/0151; A61F 2005/0153; A61F 2005/0155; A61F 2005/0165; A61F 2005/0169; A61F 5/04; A61F 5/05; A61F 5/37; A61F 5/3707; A61F 5/3715; A61F 5/3723; A61F 5/373; A61F 5/3738; A61F 5/3753; A61H 1/0274; A61H 1/0277; A43C 1/00; A43C 3/00; A43C 5/00; A41C 1/00; A41C 1/08; A41C 1/10; A41D 2400/38; A41D 3/00; A41D 1/02; A41D 13/00; A41D 13/0015; A41D 13/012; A41D 13/0518; A41D 13/0512; A41D 13/0525; A41D 31/185; A41F 9/002; A41F 1/008; A41F 1/00; A41B 3/08
USPC ....... 602/19, 5, 6, 62, 63, 12, 16, 20, 21, 23
See application file for complete search history.

(56) References Cited

U.S. PATENT DOCUMENTS

| | | | |
|---|---|---|---|
| 6,322,529 | B1 | 11/2001 | Chung |
| 8,172,779 | B2 | 5/2012 | Ingimundarson et al. |
| 8,303,528 | B2 | 11/2012 | Ingimundarson et al. |
| 8,657,769 | B2 | 2/2014 | Ingimundarson et al. |
| 8,926,537 | B2 | 1/2015 | Ingimundarson et al. |
| 8,939,925 | B2 | 1/2015 | Ingimundarson et al. |
| 8,945,034 | B2 | 2/2015 | Ingimundarson et al. |
| 9,220,625 | B2 | 12/2015 | Ingimundarson et al. |
| 9,414,953 | B2 | 8/2016 | Ingimundarson et al. |
| 9,597,219 | B2 | 3/2017 | Ingimundarson et al. |
| 10,264,835 | B2 | 4/2019 | Ingimundarson et al. |
| 10,617,552 | B2 | 4/2020 | Ingimundarson et al. |
| 2002/0068890 | A1* | 6/2002 | Schwenn .............. A61F 5/0193 602/19 |
| 2002/0074373 | A1 | 6/2002 | Heinz et al. |
| 2008/0146981 | A1* | 6/2008 | Greenwald .......... A41D 13/088 602/13 |
| 2010/0217167 | A1* | 8/2010 | Ingimundarson ....... A61F 5/028 602/19 |
| 2011/0105971 | A1 | 5/2011 | Ingimundarson et al. |
| 2012/0022419 | A1 | 1/2012 | Ingimundarson et al. |
| 2012/0204381 | A1 | 8/2012 | Ingimundarson et al. |
| 2012/0215254 | A1 | 8/2012 | Brub |
| 2013/0006158 | A1 | 1/2013 | Ingimundarson et al. |
| 2013/0184628 | A1* | 7/2013 | Ingimundarson .. A44B 13/0052 602/26 |
| 2013/0237891 | A1 | 9/2013 | Fryman et al. |
| 2014/0155798 | A1 | 6/2014 | Ingimundarson et al. |
| 2014/0200497 | A1 | 7/2014 | Ingimundarson et al. |
| 2014/0257156 | A1* | 9/2014 | Capra ................... A61F 5/0102 602/5 |
| 2014/0276300 | A1* | 9/2014 | Reinhardt ............. A61F 2/7812 602/5 |
| 2015/0014189 | A1 | 1/2015 | Stein |
| 2015/0121657 | A1 | 5/2015 | Ingimundarson et al. |
| 2015/0150705 | A1* | 6/2015 | Capra ....................... A61F 5/01 602/6 |
| 2016/0074200 | A1 | 3/2016 | Ingimundarson et al. |
| 2016/0120685 | A1* | 5/2016 | van Beek ................. A61F 5/03 602/19 |
| 2016/0310310 | A1* | 10/2016 | White ....................... A61F 5/02 |
| 2016/0324678 | A1 | 11/2016 | Ingimundarson et al. |
| 2017/0018922 | A1 | 1/2017 | Sun et al. |

FOREIGN PATENT DOCUMENTS

| | | |
|---|---|---|
| WO | 2010056217 A1 | 5/2010 |
| WO | 2010098880 A1 | 9/2010 |
| WO | 2011056217 A1 | 5/2011 |
| WO | 2012109524 A1 | 8/2012 |

OTHER PUBLICATIONS

Written Opinion (English translation, PCT/EP2017052918) dated May 23, 2017.
Chinese Office Action for application No. 2017800118965 dated May 7, 2020 with English translation.

* cited by examiner

DEFLECTION ELEMENT FOR DEFLECTING TIE CABLES IN OR ON ORTHOPEDIC OR MEDICAL INSTRUMENTS OR SPORTS INSTRUMENTS

The present invention relates to elements to deflect ropes, particularly cords, particularly tension ropes, or tension cords in or at orthopedic or at medical accessories, or athletic accessories, particularly in or at orthoses or bandages.

Belts and cords are frequently used as pull ropes or tension ropes in orthopedic or medical accessories, or athletic accessories. For instance, DE 10 2010 054 579 A1 describes an orthosis to dampen or limit the joint movement of a joint of the extremities, in which a sleeve and an abutment surface are connected with the sleeve via at least one pull rope in a force-fitted fashion.

However, such type of orthopedic accessory, medical accessory, or athletic accessory, particularly orthoses or bandages are supposed to become increasingly slimmer, lighter and thinner in the future, whereby the effectiveness should remain unchanged at least. To ensure this, it would be advantageous to replace previously used pull ropes or pull belts with ropes, particularly thin ropes, i.e. ropes with a small diameter, to guide a joint movement through the chord system of such type of orthosis or bandage for instance.

Likewise ropes and particularly cords have the advantage when compared to straps and belts that they cause less friction due to their thin and round section on the material surrounding them.

When using ropes, particularly thin ropes to introduce force, it happens, however, that the rope, particularly the chord, cuts into the wearer's skin due to their small section, thus reducing his wearing comfort.

In addition, the problem arises that orthoses in particular must be safely placed against the body in their position so that their effect may unfold as best as possible. The state of the art achieves this by tensioning belts. However, it can happen during the tensioning process that the wearer's skin gets pulled or even pinched when pulling the belts together.

Therefore, the present invention is based on the technical problem of improving the prior art's disadvantages. In particular, devices and elements should be provided that allow replacing the cords and belts, particularly tension ropes or pull ropes that are used in orthopedic or medical accessories, or athletic accessories, particularly orthoses or bandages, with ropes, particularly thin ropes, whereby in particular the ropes' force will be distributed such that the ropes will not cut into the wearer's skin. Another problem, which is the object of the present invention, consists in providing a device, which in case of a change of circumference of one of the above-mentioned accessories will not result in shifting or pinching the underlying skin tissue.

The present invention is solving the underlying technical problem particularly by means of a deflector to deflect rope in orthopedic or medical accessories, or athletic accessories, the deflector comprising at least one first subcomponent and one second subcomponent, whereby the first subcomponent and the second subcomponent are adjustable with only one degree of freedom against one another, respectively, the first subcomponent and the second subcomponent each including at least one rope guidance element to deflect rope, the first subcomponent and/or the second subcomponent including at least two edge-side guides in which the other subcomponent can slide, respectively.

The present invention is solving the underlying technical problem also particularly by means of a bodily accessory comprising a deflector, the deflector including: at least one first subcomponent and one second subcomponent, whereby the first subcomponent and second subcomponent are adjustable with only one degree of freedom against one another, respectively, the first subcomponent and second subcomponent each including at least one rope guidance element to deflect rope, the first subcomponent and/or second subcomponent including at least two edge-side guides in which the other subcomponent can slide, respectively.

The present invention relates to a deflector in particular to deflect a rope in orthopedic or medical accessories, or athletic accessories, whereby the deflector comprises at least one first subcomponent and one second subcomponent, whereby the first subcomponent and the second subcomponent are adjustable with only one degree of freedom, respectively, against one another, and whereby the first subcomponent and the second subcomponent exhibit at least one rope guidance element, respectively, to deflect the rope.

It is preferred that the subcomponents consist of a dimensionally stable material, particularly plastic or metal. A material having low friction characteristics will preferably be selected for the shells.

A deflector is attached in or at an orthopedic or medical accessory or athletic accessory, especially in or at an orthosis or bandage, and is particularly a component of an orthopedic or medical accessory, or athletic accessory, particularly of an orthosis or bandage.

It could be seen that such type of deflection elements from two subcomponents, which are kept against one another in an adjustable manner, particularly shell-shaped subcomponents, and in addition thereto, at least one, particularly two rope guidance elements to deflect a rope, respectively, particularly a chord, allow, when using a rope, particularly a chord in a medical accessory, orthopedic accessory, or athletic accessory, particularly in an orthosis or bandage, a replacement of pull ropes or tension ropes used there together with ropes, particularly cords, and a deflection of these ropes, particularly cords is possible, without the ropes, particularly cords, cutting into the accessory wearer's skin. This is also achieved in particular by means of the subcomponents extensively covering the wearer's skin in their preferred shell-form, and that in the ropes', particularly the cords' deflecting area, cutting into the skin will be avoided by means of an extensive force distribution.

In addition, the deflector according to the invention with its subcomponents that are adjustable against one another, has the technical advantage that the rope can be guided across the rope guidance element of both subcomponents so that the rope development will be extended against one another in the deflector and the rope will consequently be tensed when pushing the two subcomponents apart. Moreover, both subcomponents slide against each other so that the wearer's skin located under the deflector will not be displaced or pinched.

In a preferred embodiment of the invention, the deflector exhibits a fixating device through which the one degree of freedom can be blocked, respectively. In a preferred embodiment of the invention, the fixating device is a plug element that is plugged between the first subcomponent and the second subcomponent.

The advantage of such type of fixating device is that when fixating the fixating mechanism, for instance, when plugging the plug element between the first and the second subcomponent, they no longer can move together, so that the rope remains tensed in the deflector.

In a preferred embodiment of the invention, the first subcomponent and/or the second subcomponent exhibit/s at least two edge-side guides in which the other subcomponent can slide, respectively. In a preferred embodiment of the invention, the guides are formed as groove conductions.

Edge-side guides, particularly groove conductions allow in an advantageous manner that both subcomponents be dislocated against one another with only one degree of freedom by means of sliding, whereby they are fixated with each other at the same time, thus preventing shifts to other degrees of freedom.

In a preferred embodiment of the invention, both subcomponents have a plate-shaped base body, respectively, from which protrudes at least one rope guidance element and at least two edge-side guides on one side.

A plate-shaped base body of both subcomponents results in an advantageous extensive shell form. Both plates are held together by means of the edge-side guides with somewhat of a clearance so that the rope guidance elements to deflect the rope may be located between the two plates, and so that the rope can therefore be guided between the two plates.

In a preferred embodiment of the invention, both subcomponents form an interior space whose size is changeable by means of shifting both subcomponents against one another, whereby the rope guidance elements protrude into the interior space.

In a preferred embodiment of the invention, the shift of both subcomponents towards each other takes place in a circular arc and the shift changes a circular segment's arc length.

In this embodiment of the invention, the deflector is particularly suitable when using an orthopedic or medical accessory in the area of an extremity, but also in the upper body's area. The circular arc's radius can be adapted in an advantageous manner to the radius of said extremity or to the upper body. As a consequence, the deflector can partially encompass the extremity or the upper body in an advantageous manner. When pushing apart both subcomponents, the encompassed part will be enlarged accordingly.

In a preferred embodiment of the invention, the first subcomponent and/or the second subcomponent exhibit/s at least one hole through which to pass the rope.

In a preferred embodiment of the invention, the deflector comprises a rope, particularly a chord. In a preferred embodiment of the invention, the rope is a cord, in other words, a rope having a thin diameter. Experts know of suitable cords and suitable materials for such type of cords.

In a preferred embodiment of the invention, the first subcomponent and the second subcomponent, respectively, exhibit two rope guidance elements to deflect the rope, whereby the rope is first deflected through the first rope guidance element of the first subcomponent, then deflected through the first rope guidance element of the second subcomponent, then deflected through the second rope guidance element of the first subcomponent, and then deflected through the second rope guidance element of the second subcomponent.

As a consequence, a rope pull system is created, whereby a stronger tension of the rope can be induced by means of pushing apart the subcomponents. Using the number of rope guidance elements it can be determined in an advantageous manner which rope length should be pulled in into the deflector when pulling apart the subcomponents, and thus, to what extent the rope will be tensed.

In a preferred embodiment of the invention, shifting both subcomponents against one another causes the rope to be tensed.

In a preferred embodiment of the invention, tensing the rope causes a shifting of both subcomponents against each other.

And it can be provided that tensing the rope in another area of the accessory will result in pushing together the subcomponents. For instance, it can be used in a movement-limiting orthosis when the subcomponents exhibit arched lateral areas, which protrude when pushing together the subcomponents and which are consequently encompassing an extremity more strongly.

The other way around, pulling apart the subcomponents can be used to tense a rope, whereby the subcomponents can be fixated by means of a fixating device in a position when pushed apart, so that the rope remains tensed.

In a preferred embodiment of the invention, the rope enters into the deflector and exits the deflector again after the deflection.

In an alternative embodiment of the invention, the rope enters into the deflector and one of its ends is attached at the deflector after the deflection.

It can be provided that the rope be led from another area of an accessory to the deflector, that it is brought into the deflector, that it is deflected there, and then again guided out of the deflector and then guided to an additional area of the accessory. Alternatively, it can also be provided that the rope is attached to a part of a subcomponent of the deflector, that it is deflected by means of the deflector, and that it simply exits the deflector and is led to an additional area of the accessory.

The present invention also relates to an orthopedic accessory, a medical accessory, or an athletic accessory, comprising a deflector according to the invention.

In a preferred embodiment of the invention, the orthopedic accessory, the medical accessory, or the athletic accessory exhibit a tension rope to which the deflector is assigned.

In a preferred embodiment of the invention, the orthopedic accessory is an orthosis.

The orthosis could be an arm orthosis, a leg orthosis, or a back orthosis for instance. It is preferred that it is an orthosis for the extremities. For instance, it could be an orthosis exercising a supporting or movement-sliding function, particularly an orthosis that dampens or limits the flexion or stretching movement of a joint of the extremities, such as an elbow joint or a knee joint. Such an orthosis is known from the DE 10 2010 054 579 A1 for instance. An expert can readily replace the pull belts depicted there with ropes, particularly cords, and the pressure introduction section shown there by means of a deflector according to the invention. The present invention therefore preferably relates to an orthosis, which was modified accordingly, as described in DE 10 2010 054 579 A1. The object of DE 10 2010 054 579 A1 is therefore included in the present disclosure.

In a preferred embodiment of the invention, the orthosis is an orthosis to dampen or limit the joint movement of a joint of the extremities, exhibiting a sleeve encompassing the extremity below the joint, which is coupled with an abutment surface that can be applied above the extremity, whereby at least one pull rope extends from the abutment surface to the sleeve, which is connected with the abutment surface and the sleeve in a force-fitted fashion, whereby the pull rope is connected with the sleeve via a deflector according to the invention, and whereby the deflector is formed as a pressure introduction section of the sleeve, and whereby the pull rope is arranged thus that it is tensible in the applied condition of the orthosis through the joint movement of the extremity to thus apply compression onto the underlying soft tissue area of the extremity to dampen or limit the joint's movement.

In a preferred embodiment of the invention, the pull rope progresses twofoldly in the orthosis and crosses over from the abutment surface to the sleeve's pressure introduction section, and is deflected at the pressure introduction section by means of the deflector according to the invention.

In a preferred embodiment of the invention, the abutment surface is formed as a second sleeve.

In a preferred embodiment of the invention, the first sleeve and/or the second sleeve constitute flexible sleeve belts, which can be preferably opened and tightened by means of a hook and loop fastener.

In a preferred embodiment of the invention, the sleeve and abutment surface are set up on knitted textile fabric.

In a preferred embodiment of the invention, the pull rope may be tensed in the area of the abutment surface by means of a roll-up element. In addition, the pull rope is tensed by means of the roll-up element in this preferred embodiment of the invention, by which both subcomponents of the deflector can be pushed together in the area of the first sleeve, and whereby the shift of both subcomponents to each other preferably takes place in a circular arc and whereby the deflector encompasses the extremity more strongly.

Preferred embodiments of the invention also result from the sub-claims.

The present invention is explained in more detail and by way of example on the basis of the figures, whereby the figures and corresponding explanation are not to be interpreted as being restrictive.

Figure 2:
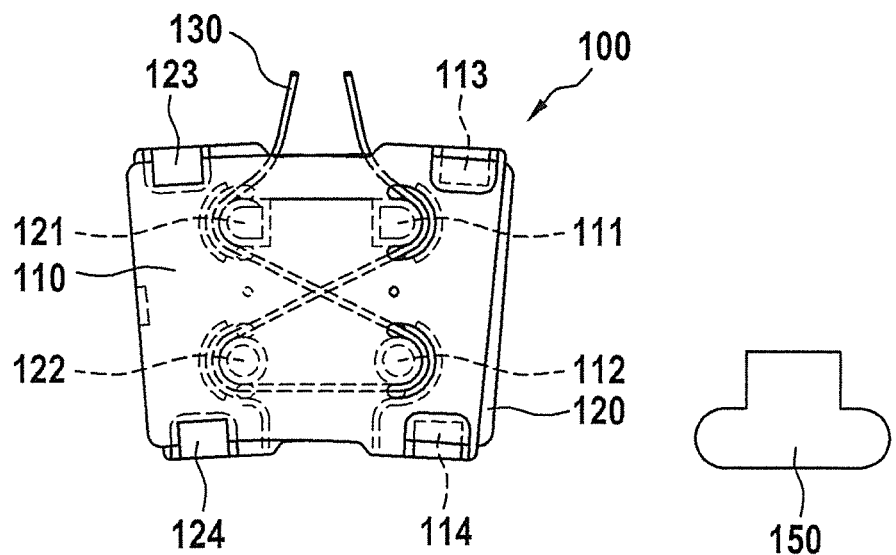
Figure 3:
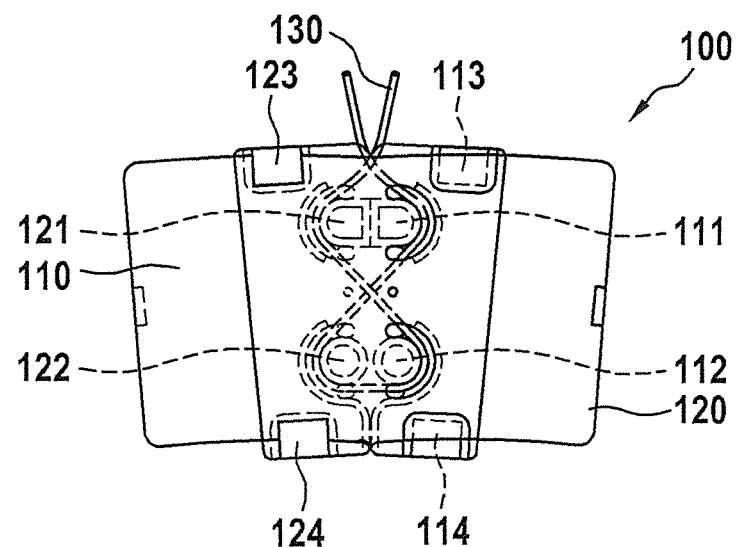
Figure 4:
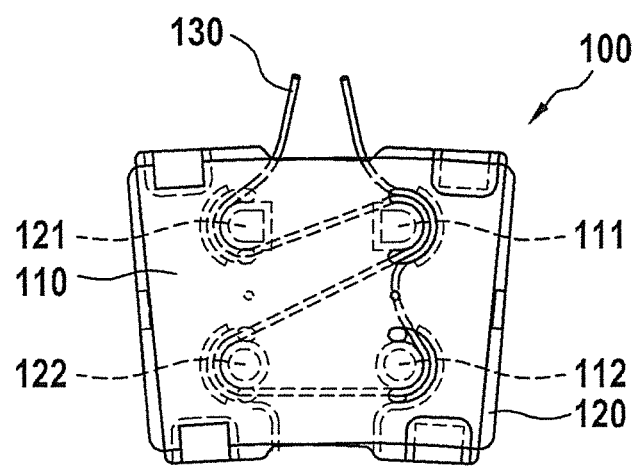
Figure 5:
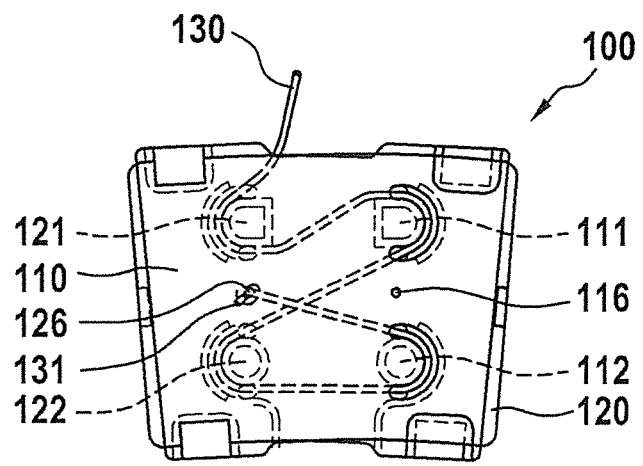
Figure 6:
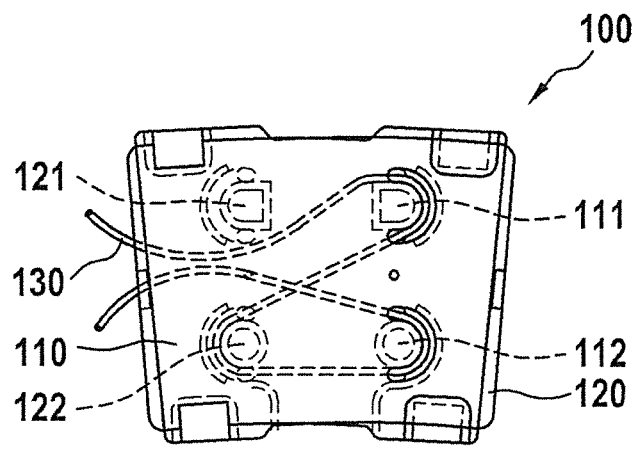
Figure 7:
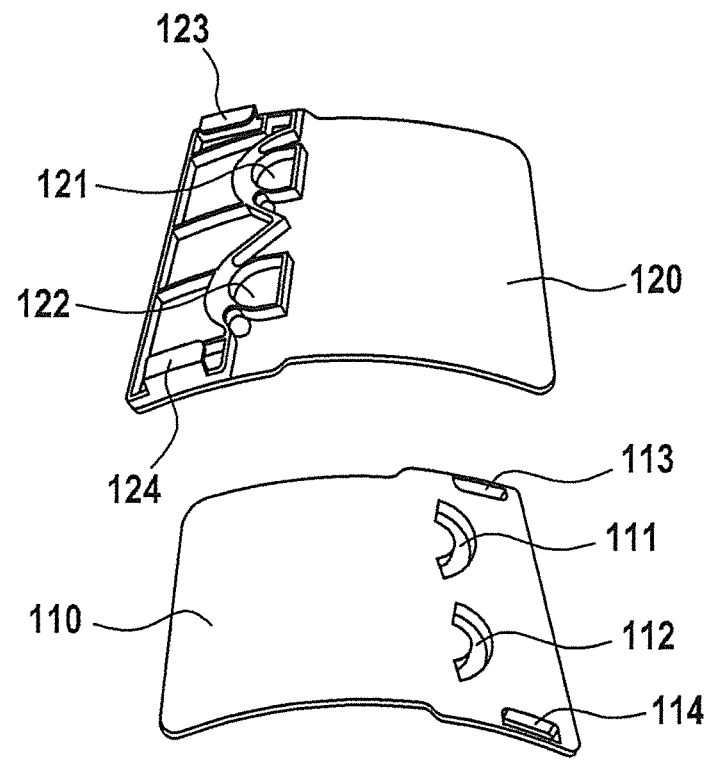
Figure 8:
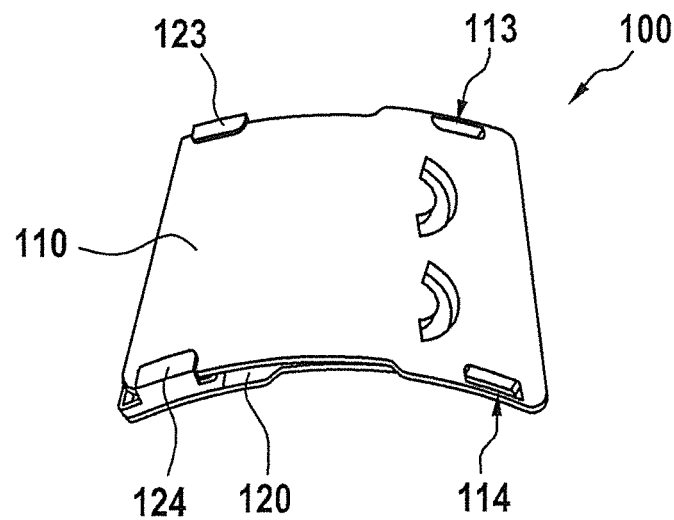
Figure 9:
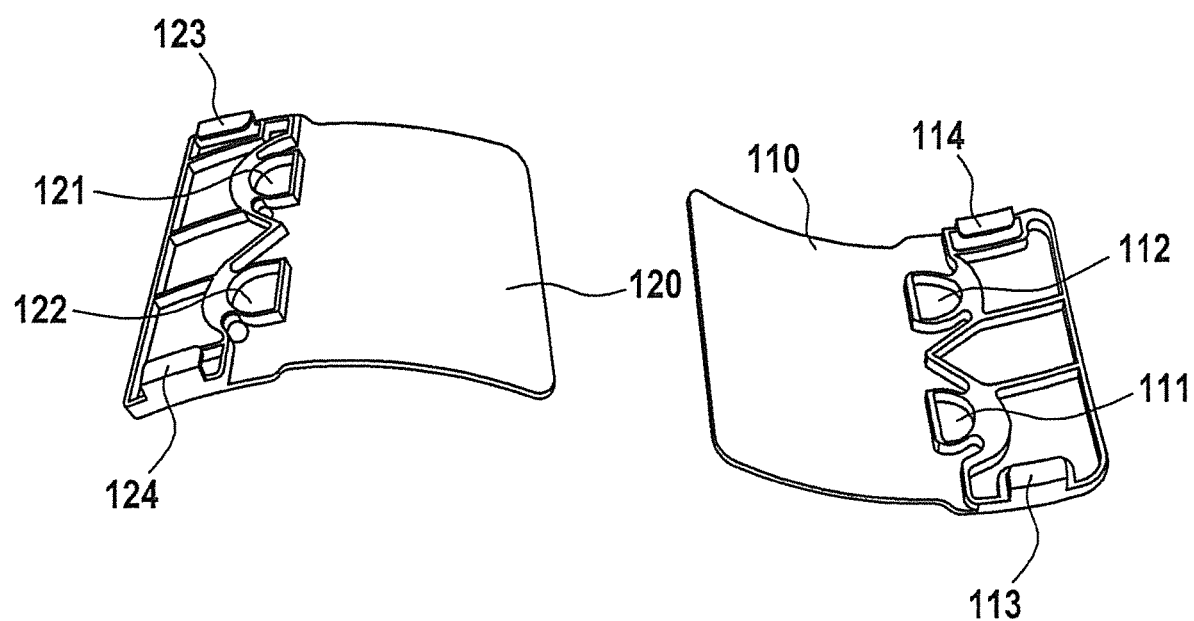
Figure 10:
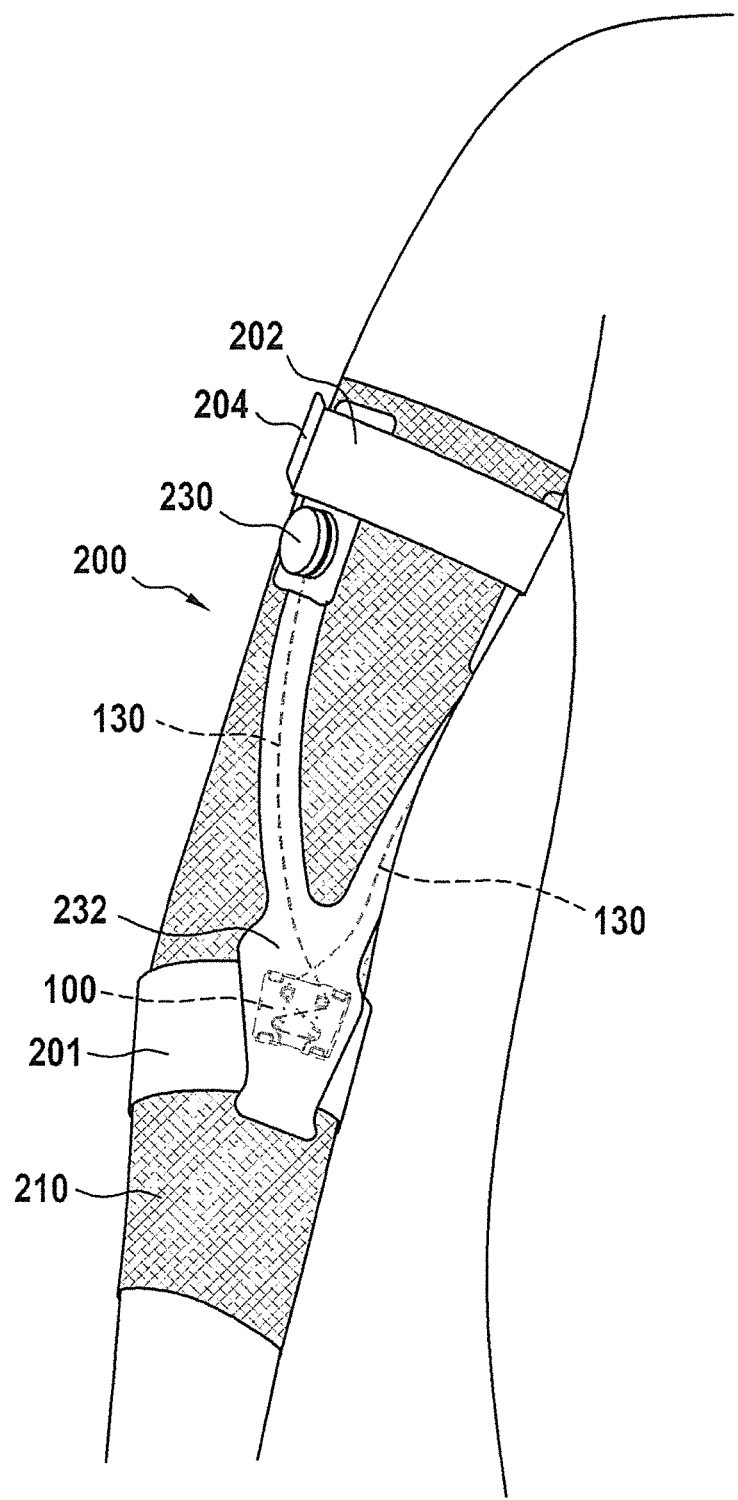
Figure 11:
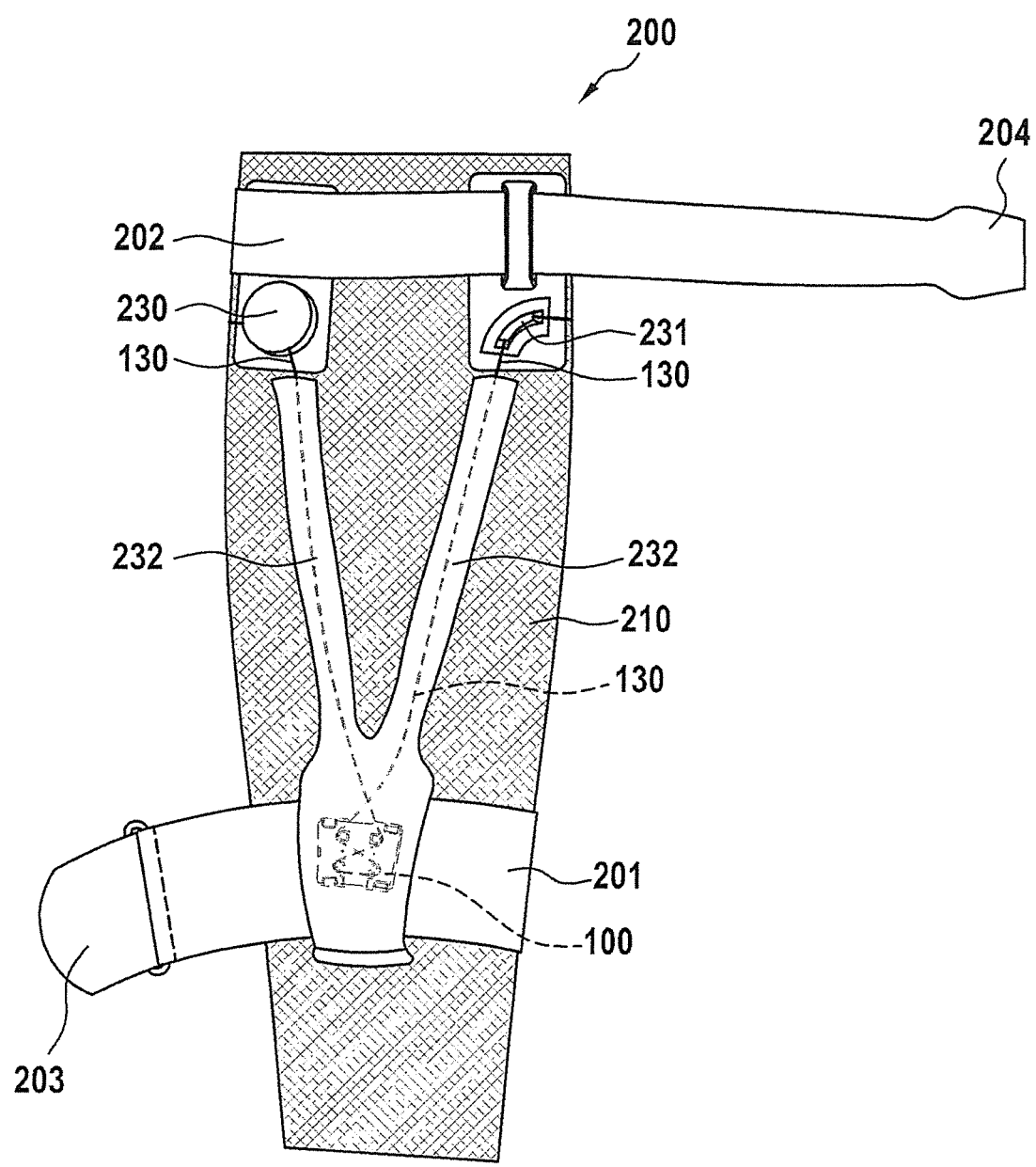
Figure 12:
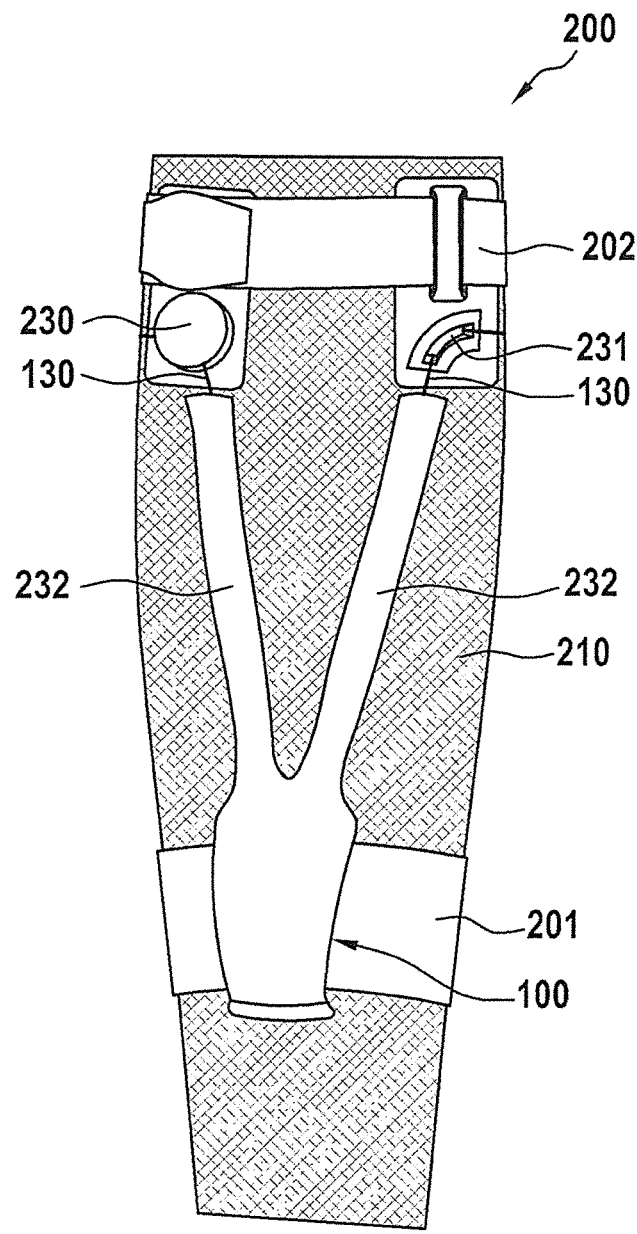
Figure 13:
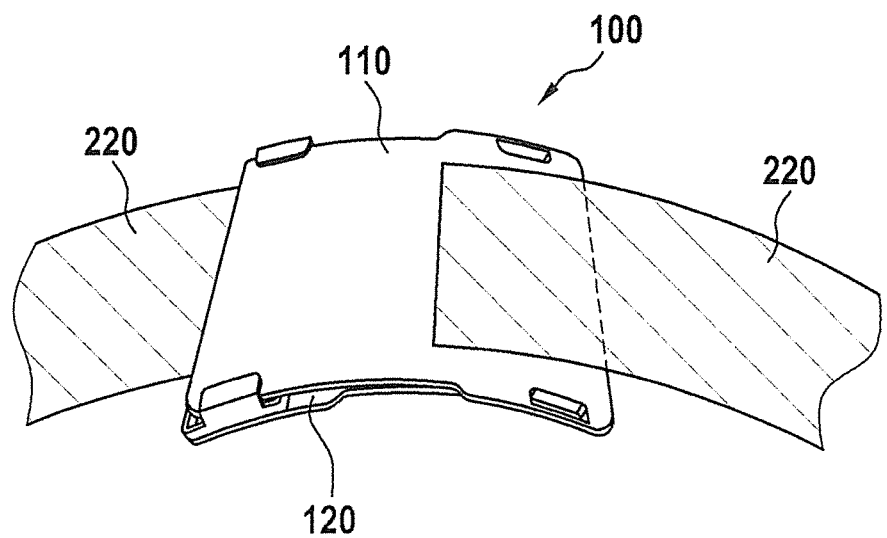
Figure 14:
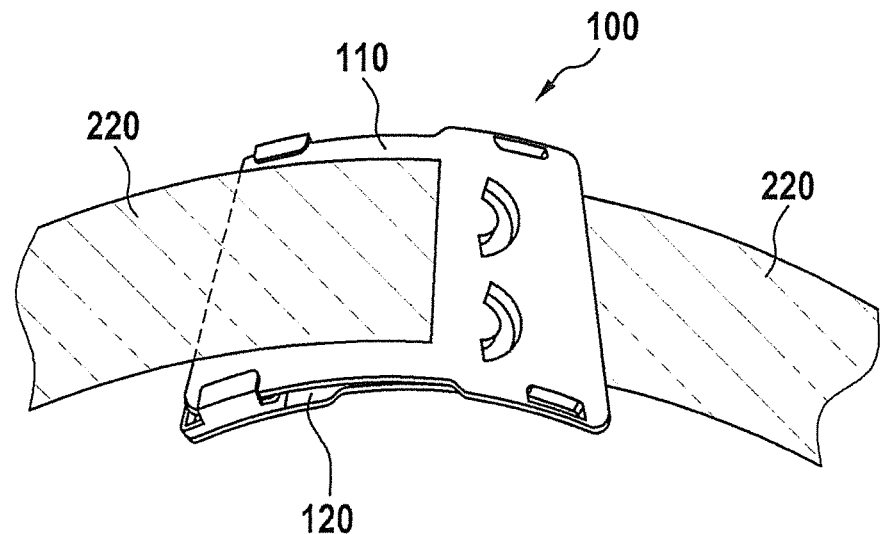

The following is depicted:

FIG. 1 a deflector according to the invention having an inserted plug element;

FIG. 2 the deflector according to the invention of FIG. 1 with the pulled-out plug element;

FIG. 3 the deflector according to the invention of FIG. 2 with subcomponents that are pushed together;

FIG. 4 deflector according to the invention with an alternative deflection of the chord;

FIG. 5 deflector according to the invention with an additional alternative deflection of the chord;

FIG. 6 deflector according to the invention with an additional alternative deflection of the chord;

FIG. 7 the two subcomponents of a deflector according to the invention;

FIG. 8 an additional view of a deflector according to the invention;

FIG. 9 the two subcomponents of a deflector according to the invention;

FIG. 10 an orthosis according to the invention to dampen or limit the joint movement of an elbow;

FIG. 11 an additional view of the orthosis from FIG. 10;

FIG. 12 an additional view of the orthosis from FIG. 10;

FIG. 13 the deflector from FIG. 8 with a belt attached at the subcomponents;

FIG. 14 the deflector from FIG. 8 with a belt that was alternatively attached at the subcomponents.

Depicted in FIGS. 1 through 9 are two form-stable merging subcomponents (110, 120) in the shape of shell elements. The shell elements can be arranged in a flat manner or they can be anatomically preformed as a cylinder segment or as a cone segment. Each shell element exhibits two rope guidance elements (111, 112, 121, 122) for chord guidance. Force-introducing chord (130) progresses in the intermediary space of the shell elements. The chord can proceed between den shells in ring-form, parallel, cross-over or in a type of pulley. In addition to a linear application of force, the tensioning force can be deflected by means of the shells by 10° through 170°, preferably by about 90°. The tension shells themselves can be attached at a bandage or at orthosis (200) in a force-fitted fashion, as is depicted for instance in FIGS. 10 through 12. Should the length of chord (130) be changed, shell elements (11, 120) are pulled on top of each other and the bandage or orthosis (200) is pulled towards the body. As the shells form a closed system form, there exist no gaps in which the skin could be pinched when tensing or into which the chord could cut in. In the case of knee orthoses, the tension shells could form the frame of the orthosis at the same time for instance. The tensioning shell technology allows dampening movements by pushing together the shells, and by the wearer's own musculature acting as a damper. The pushing together of the elements by means of a fixating device, for instance plug element (150) in the fashion of a splint can be halted at the start of the treatment. This splint can be removed again during the course of a further treatment and the damping effects can be utilized again.

The length and width of the adjustment path and thus the damping path are adaptable by means of scaling tension shells (110, 120) to the respective product-specific requirement of the orthoses or bandages.

FIG. 1 depicts a deflector according to the invention (100) with inserted plug element (150). Deflector (100) serves to deflect chord (130) in orthopedic or medical accessories, or athletic accessories, for instance the orthosis depicted in FIGS. 10 through 12, to dampen or limit an elbow joint's movement. Deflector (100) comprises one first subcomponent (110) and one second subcomponent (120), whereby first subcomponent (110) and second subcomponent (120) exhibit a plate-shaped base body, respectively, and which are adjustable against one another with only one degree of freedom. First subcomponent (110) exhibits two rope guidance elements (111, 112), and the second subcomponent exhibits two rope guidance elements (121, 122). The four rope guidance elements (111, 112, 121, 122) serve to deflect chord (130). First subcomponent (110) exhibits two edge-side guides (113, 114) that encompass second subcomponent (120) as groove conductions. Likewise, second subcomponent (120) exhibits two edge-side guides (123, 124) that encompass first subcomponent (110) as groove conductions. Thus, a subcomponent can slide, respectively, in the edge-side guides of the other subcomponent.

Both subcomponents (110, 120) form an interior space whose size is alterable by means of shifting both subcomponents against one another: rope guidance elements (111, 112, 121, 122) protrude into the interior space.

Both subcomponents (110, 120) are depicted in FIG. 1 in a position after having been pushed apart. Consequently, both rope guidance elements (111, 112) of first subcomponents (110) are at the largest distance possible from the two rope guidance elements (121, 122) of the second subcomponents (110), so that chord (130), which is alternatively deflected from a rope guidance element of the first subcomponent and from a rope guidance element of the second subcomponent progresses on a long path in deflector (100), so that a lot of chord will be consumed, whereby the chord will be tensed when it is not attached at an abutment surface at its ends that are not shown. To ensure that this tension remains maintained, a fixating device formed as plug element (150) is inserted between both subcomponents (110, 120) so that they will not be pushed together or so that they will not be able to pull themselves together, and the one degree of freedom will consequently be blocked.

In FIG. 2, plug element (150) is pulled out so that both subcomponents (110, 120) continue to remain in their position of being pulled apart but where they can be pushed together along the one degree of freedom, for instance by means of pulling forces acting via chord (130). Again, four of rope guidance elements (111, 112, 121, 122) and four edge-side guides (113, 114, 123, 124) of deflector (100) can be seen.

FIG. 3 depicts deflector (100) with both subcomponents (110, 120) in a position in which they are pushed together, whereby this position is achieved by both subcomponents (110, 120) sliding in edge-side guides (113, 114,123,124) of the other subcomponents, respectively. In their position of being pushed together, both rope guidance elements (111, 112) of first subcomponents (110) are at the smallest possible distance from both rope guidance elements (121, 122) of second subcomponents (110) so that chord (130), which is alternatively deflected from a rope guidance element of the first subcomponent and from a rope guidance element of the second subcomponent, and which progresses on a short path in deflector (100) so that very little chord is being used and so that the chord will no longer be tensed when it is attached to an a abutment surface at its ends that are not shown.

And in the embodiment of the invention of deflector (100) according to FIGS. 1 through 3, it can be provided that shifting both subcomponents (110, 120) against one another will result in tensing chord (130), and it can be also provided that tensing chord (130) will result in shifting both subcomponents (110, 120) against one another.

As depicted in FIGS. 1 through 3 as well, it has also been provided in FIGS. 4 through 6 that the chord is first deflected through the first rope guidance element of a subcomponent, then through the first rope guidance element of the other subcomponent, and that it is then deflected through the second rope guidance element of a subcomponent, and that it is then deflected through the second rope guidance element of the other subcomponent.

FIGS. 4 through 6 depict alternative embodiments of the invention of deflector (100), whereby the setup of deflector (100) is the same as in FIGS. 1 through 3, in other words, both subcomponents (110, 120) also exist with rope guidance elements (111, 112, 121, 122). While chord (130) in FIGS. 4 and 6 enters into deflector (100) and exits deflector (100) again after deflecting, one end (131) in FIG. 5 is attached to one of the subcomponents, which in this case is second subcomponent (120). Therefore, plate-shaped subcomponents (110, 120) also exhibit additional holes (116, 126) through which chord (130) may alternatively enter and exit deflector (100) as well.

A suitable angle to introduce force can be selected in an advantageous manner by means of the various chord guide options.

FIGS. 7 through 9 depict an additional embodiment of the invention of deflector (100) according to the invention including subcomponents (110, 120), which once more exhibit rope guidance elements (111, 112, 121, 122) and edge-side guides (113, 114, 123, 124). While in FIGS. 7 and 9, subcomponents (110, 120) are depicted as individual parts, assembled deflector (100) can be seen in FIG. 8, without a chord, however. The chord's progress preferably occurs as shown in FIGS. 1 through 3, but alternatively in a different manner, for instance as shown in FIGS. 4 through 6. In the depicted embodiment of the invention, the shift of both subcomponents (110, 120) towards each other occurs in a circular arc so that and by means of a shift the arc length of a circular segment will be changed. Such type of deflector can be used in an advantageous fashion at an extremity, for instance at an arm, whereby the circular segment's radius has just about the dimension of the extremity's radius. Such type of embodiment of the invention is also used in the orthosis depicted in FIGS. 10 through 12 to dampen or limit the joint movement of an elbow.

Preferably, the deflection element can be used therefore in a "throw-orthosis", i.e. an arm orthosis which is supposed to limit the extension of the arm when throwing a ball for instance so that the limb will not be hyper-extended. Such orthosis is shown in FIGS. 10 through 12. By realizing the extension movement of the limb, the circumference of the sleeve will be reduced via the rope. The further the extension is completed, the harder the sleeve's grip, thus preventing a full arm extension and its own upward slide on the lower arm as it were. Thereby deflector (100) according to the invention permits that an appropriately strong force of the rope may distribute itself extensively, to not cut itself and for the rope to not cut into the underarm.

Orthosis (200) from FIGS. 10 through 12 therefore serves to dampen or limit an arm's joint movement and exhibits first sleeve (201) encompassing an underarm, which is coupled to an abutment surface, which can be applied at the upper arm, and which is implemented as second sleeve (202). Double pull rope (130), which is also guided in a cross-over fashion, extends from first sleeve (201) to second sleeve (202) which is connected with the two sleeves in a force-fitted manner, whereby the pull rope is connected via deflector (100) according to the invention with first sleeve (201). Thus, deflector (100) is formed as a pressure introduction section of first sleeve (201), whereby pull rope (130) is arranged such that it is tensible in the applied condition of orthosis (200) through the elbows' joint movement to thus exercise a compression on the underlying deflector (100) onto the underlying soft tissue area of the lower arm in order to dampen or limit the elbow's movement. Sleeves (201, 202) are set up on textile knitted fabric (210).

Pull rope (130) can be tensed in the area of second sleeve (202) through roll-up element (230). Thereby, both ends of pull rope (130) are connected with roll-up element (230) and are tensed or loosened when turning roll-up element (230). To guide pull rope (130) to roll-up element (230) additional simple deflect elements (231) from prior art may be used. Likewise, pull rope (130) may progress in rope channels (232), which for instance were welded on, sewn on, or glued on textile knitted fabric (210). In FIG. 12, rope channels (232) cover pull rope (130) and deflector (100). Consequently, deflector (100) and pull rope (130) are drawn in FIGS. 10 and 11 as a dashed line.

Sleeves (201, 202) are reversibly affixable by being provided with hook and loop fastener (203, 204). FIG. 11 shows opened hook and loop fasteners, and in FIGS. 10 and 12 the hook and loop fasteners are closed.

FIGS. 13 and 14 show arched deflector (100) from FIG. 8. Belt (220) is attached to both subcomponents (110, 120), respectively, which for instance can encompass an extremity.

In FIG. 13 belt (220) is attached at subcomponents (110, 120) in such manner that it will be pulled together when pushing together subcomponents (110, 120) so that the belt's size will be reduced. In FIG. 14 belt (220) is attached to subcomponents (110, 120) in such fashion, that the belt's size increases when pushing apart subcomponents (110, 120). Pushing together subcomponents (110, 120) can be realized especially when tensing a tension rope that is not depicted, for instance as a consequence of a movement of the joints of the extremities of the extremity that is encompassed by belt (220).

Therefore, selecting the positioning of a belt on the deflector according to the invention simply achieves the desired effect by means of pushing together the subcomponents, thus reducing the belt size, which results in a tighter fit of the belt at the extremity, or an enlargement of the belt size, which results in a more loose fit of the belt at the extremity.

As an alternative to a continuous belt, the subcomponents can also be connected with different belts, respectively, which end on a basic kitted tissue or another orthosis element, for instance.

The invention claimed is:

1. A deflector to deflect rope in orthopedic or medical accessories, or athletic accessories, the deflector comprising:
at least one first subcomponent; and
at least one second subcomponent discrete from the at least one first subcomponent, the first subcomponent and the second subcomponent having only one degree of freedom to enable the first and second subcomponents to move relative to one another, the first subcomponent and the second subcomponent each including at least one rope guidance element to deflect rope,
the first subcomponent and the second subcomponent each including at least two edge-side guides in which the other subcomponent is disposed, wherein the first subcomponent and the second subcomponent are arranged in an overlapping fashion such that the first subcomponent and/or the second subcomponent can slide in the at least two edge-side guides as the first and second subcomponents move relative to one another,
wherein each of the first and second subcomponents has a plate-shaped base body, respectively, from each of which protrudes the respective at least one rope guidance element and the respective at least two edge-side guides on one side thereof, wherein the one side of the first subcomponent faces the one side of the second subcomponent.

2. The deflector according to claim 1, wherein the deflector includes a fixating device through which the one degree of freedom can be blocked.

3. The deflector according to claim 1, wherein both the first and second subcomponents form an interior space, a size of the interior space being adjustable by shifting both the first and second subcomponents against one another and wherein each of the at least one rope guidance elements protrudes into the interior space.

4. The deflector according to claim 1, wherein shifting of both the first and second subcomponents towards each other occurs in a circular arc.

5. The deflector according to claim 1, wherein the first subcomponent and/or the second subcomponent define or defines at least one hole.

6. The deflector according to claim 5, further comprising a rope that passes through the at least one hole.

7. The deflector according to claim 6, wherein the first subcomponent and second subcomponent include, respectively, two rope guidance elements to deflect the rope and wherein the rope is first deflected through a first rope guidance element of the first subcomponent, then through a first rope guidance element of the second subcomponent, and then deflected through a second rope guidance element of the first subcomponent, and then deflected through a second rope guidance element of the second subcomponent.

8. The deflector according to claim 7, wherein shifting both the first and second subcomponents against one another tenses the rope.

9. The deflector according to claim 8, wherein tensing the rope will result in a shift of both the first and second subcomponents against one another.

10. The deflector according to claim 7, wherein the rope enters into the deflector and exits the deflector after the rope is deflected.

11. The deflector according to claim 10, wherein the rope enters into the deflector and wherein the rope is attached with one end at the deflector after the rope is deflected.

12. The deflector according to claim 1, wherein the at least one first subcomponent has a first free end and a second free end, the at least one first subcomponent defining a length that extends between the first and second free ends of the at least one first subcomponent, and wherein the at least one second subcomponent has a first free end and a second free end, the at least one second subcomponent defining a length that extends between the first and second free ends of the at least one second subcomponent.

13. A bodily accessory comprising:
a deflector, the deflector including:
at least one first subcomponent; and
at least one second subcomponent discrete from the at least one first subcomponent, wherein the first subcomponent and the second subcomponent are adjustable with only one degree of freedom against one another, respectively, the first subcomponent and the second subcomponent each including at least one rope guidance element to deflect rope,
the first subcomponent and the second subcomponent each including at least two edge-side guides in which the other subcomponent is disposed, wherein the first subcomponent and the second subcomponent are arranged in an overlapping fashion such that the first subcomponent and/or the second subcomponent can slide in the at least two edge-side guides,
wherein each of the first and second subcomponents has a plate-shaped base body, respectively, from each of which protrudes the respective at least one rope guidance element and the respective at least two edge-side guides on one side thereof, wherein the one side of the first subcomponent faces the one side of the second subcomponent.

14. The bodily accessory according to claim 13, wherein the bodily accessory includes a tension rope in contact with the deflector.

15. The bodily accessory according to claim 13, wherein the bodily accessory is an orthopedic accessory, or a medical accessory, or an athletic device.

16. The bodily accessory according to claim 15, wherein the bodily accessory is an orthopedic accessory, the orthopedic accessory being an orthosis that dampens or limits the joint movement of a joint.

17. The bodily accessory according to claim 16, wherein the orthosis to dampen or limit the joint movement of the joint includes a sleeve encompassing an extremity below the joint, the sleeve being coupled with an abutment surface that can be applied above the extremity, wherein at least one pull rope extends from the abutment surface to the sleeve, the at least one pull rope being connected in a force-fitting manner with the abutment surface and the sleeve, wherein the at least one pull rope is connected via the deflector with the sleeve, and wherein the deflector is formed as a pressure introduction section of the sleeve, and wherein the at least one pull rope is arranged in such fashion that the orthosis can be tensed in an applied condition thereof by the joint movement of the extremity to thus exercise a compression via the deflector onto an underlying soft tissue area of the extremity in order to dampen or limit any joint movements.

18. The bodily accessory according to claim 17, wherein the at least one pull rope progresses twofoldly and is crossed over by the abutment surface to the pressure introduction section of the sleeve, and is deflected at the pressure introduction section by the deflector.

19. The bodily accessory according to claim 17, wherein the abutment surface is formed as a second sleeve.

20. The bodily accessory according to claim 17, wherein the sleeve and the abutment surface are disposed on a textile knitted fabric.

21. The bodily accessory according to claim 17, wherein the pull rope in an area of the abutment surface can be tensed by a roll-up element.

\* \* \* \* \*